(12) United States Patent
Forster et al.

(10) Patent No.: US 8,500,961 B2
(45) Date of Patent: Aug. 6, 2013

(54) DISTILLATION OF IONIC LIQUIDS USING AN AUXILIARY DISTILLATION AGENT

(75) Inventors: Guenter Forster, Ludwigshafen (DE); Vijay Narayanan Swaminathan, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 7 days.

(21) Appl. No.: 13/201,743

(22) PCT Filed: Feb. 15, 2010

(86) PCT No.: PCT/EP2010/051831
§ 371 (c)(1),
(2), (4) Date: Aug. 16, 2011

(87) PCT Pub. No.: WO2010/094640
PCT Pub. Date: Aug. 26, 2010

(65) Prior Publication Data
US 2011/0297530 A1    Dec. 8, 2011

(30) Foreign Application Priority Data
Feb. 23, 2009  (EP) .................................... 09153415

(51) Int. Cl.
*B01D 3/34*    (2006.01)
(52) U.S. Cl.
USPC .................. 203/57; 203/50; 203/63; 203/100
(58) Field of Classification Search
USPC ................ 203/2, 38, 50, 57–70, 89, 98, 100; 548/341.1, 345.1, 346.1; 159/5–15; 202/81–270
See application file for complete search history.

(56) References Cited

U.S. PATENT DOCUMENTS

| | | | |
|---|---|---|---|
| 5,077,414 A * | 12/1991 | Arduengo, III | 548/335.1 |
| 2003/0186803 A1 | 10/2003 | Earle et al. | |
| 2007/0095645 A1 * | 5/2007 | Maase | 203/2 |
| 2010/0029519 A1 * | 2/2010 | Schwab et al. | 508/208 |
| 2010/0300870 A1 * | 12/2010 | Massonne et al. | 203/89 |

FOREIGN PATENT DOCUMENTS

| | | |
|---|---|---|
| DE | 103 33 239 | 3/2005 |
| WO | 91 14678 | 10/1991 |
| WO | 96 18459 | 6/1996 |
| WO | 01 77081 | 10/2001 |
| WO | 03 029329 | 4/2003 |
| WO | 2005 021484 | 3/2005 |
| WO | 2005 068404 | 7/2005 |
| WO | 2009 027250 | 3/2009 |

OTHER PUBLICATIONS

MacFarlane, et al., "Lewis base ionic liquids," Chemical Communications, XP-002483141, pp. 1905-1917 (2006).
Earle, et al., "The distillation and volatility of ionic liquids," Nature Publishing Group, XP-002543390, pp. 831-834 (2006).
International Search Report issued Aug. 5, 2010 in PCT/EP10/051831 filed Feb. 15, 2010.

* cited by examiner

*Primary Examiner* — Duane Smith
*Assistant Examiner* — Thomas McKenzie
(74) *Attorney, Agent, or Firm* — Oblon, Spivak, McClelland, Maier & Neustadt, L.L.P.

(57) ABSTRACT

Method of distilling mixtures comprising salts having a melting point of less than 200° C. at 1 bar (ionic liquids), wherein the mixtures additionally comprise an organic compound (called distillation aid below) which
  is not ionic
  has a molecular weight of less than 5000
  has a boiling point which is at least 5° C. higher compared with the ionic mixtures included in the mixture.

24 Claims, No Drawings

DISTILLATION OF IONIC LIQUIDS USING AN AUXILIARY DISTILLATION AGENT

The invention relates to a method of distilling mixtures comprising salts having a melting point of less than 200° C. at 1 bar (ionic liquids), wherein the mixtures additionally comprise an organic compound (called distillation aid below) which is not ionic, has a molecular weight of less than 5000 and has a boiling point which is at least 5° C. higher compared with the ionic mixtures included in the mixture.

Salts having a melting point of less than 200° C., in particular a melting point of less than 100° C., are referred to as ionic liquids. Ionic liquids which are liquid at room temperature are of particular interest. It was believed for a long time that such ionic liquids could not be distilled, since it was assumed that they ultimately have no vapor pressure.

In February 2006, Martyn J. Earle, Jose M. S. S. Esperanca et al published an article about the distillation of volatile ionic liquids in a bulb tube apparatus in Nature, Vol. 439, 2006, pages 831 to 834. However, ionic liquids comprising halides, sulfates or carboxylates decompose and could not be distilled.

WO 2005/068404 describes the distillation of ionic liquids, including those having halides and acetates as anion. A significant aspect here is that the ionic liquids can, owing to an equilibrium reaction, also be present as neutral compounds, i.e. not as salt. As a result of the distillation, these neutral compounds are removed. Continual restoration of the equilibrium state results in the entire ionic liquid distilled in the form of the neutral compounds. In the case of ionic liquids having nitrogen-comprising, heterocyclic ring systems as cation and, for example, halides or carboxylates as anion, a corresponding equilibrium state can be established if at least one nitrogen atom of the ring system is not substituted by an organic group and is thus available for an equilibrium reaction of the anion. Accordingly, only the chlorides of 1-ethylimidazole or 1-methylimidazole are distilled in the examples of WO 2005/068404.

Douglas R. MacFarlane, Jennifer M. Pringle et al., Chem. Commun., 2006, pages 1905 to 1917, also disclose a distillation of ionic liquids. Here, the ability to be distilled is based on an equilibrium reaction in which the cation and anion of the ionic liquid are present as neutral acid and base. As indicated above, the neutral compounds are withdrawn from the equilibrium state and distilled. In this way, it is possible to distill imidazolium acetates in which a nitrogen atom of the heterocyclic ring system is present in protonated form (HMIM acetate in Table 4 of the article).

Ionic liquids are generally not consumed but only contaminated during use. Since they are high-priced materials, there is a need for particularly effective and advantageous methods of working up and separating the anionic liquids from the mixtures obtained in use. When ionic liquids are used for dissolving cellulose, mixtures comprising lignins or cellulose derivatives, for example, are formed. Furthermore, inexpensive processes for preparing ionic liquids are known, but these form relatively nonvolatile by-products, the reaction products obtained are discolored because of these by-products and generally appear black. Such processes are described, for example, in WO 2005/021484 (carbonate method) or in WO 91/14678 (Arduengo process). Here too, there is a need for particularly effective and advantageous methods of working up and separating the ionic liquids from the mixtures obtained in the preparation.

The earlier patent application DE 102007041416.3, unpublished at the priority date of the present invention, already describes a process for separating ionic liquids by molecular distillation.

It is therefore an object of the present invention to provide a simple and effective method of purifying or working up ionic liquids or the mixtures obtained in their preparation and/or use.

We have accordingly found the method defined at the outset.

Ionic Liquid

The ionic liquid according to the invention is a salt which is composed of at least one cation and at least one anion and has a melting point at atmospheric pressure (1 bar) of less than 200° C., in particular less than 100° C., preferably less than 75° C. It is very particularly preferably a salt which is liquid at room temperature (21° C.) and atmospheric pressure (1 bar).

The cation of the ionic liquid is, according to the invention, a heterocyclic ring system having at least one nitrogen atom as constituent of the ring system. All nitrogen atoms of the ring system bear an organic group as substituent. Protonation of these nitrogen atoms is therefore not possible. The substituent (or the substituents in the case of multiple nitrogen atoms) is preferably an organic group which comprises from 1 to 20 carbon atoms, in particular from 1 to 10 carbon atoms. It is particularly preferably a hydrocarbon group which has no further heteroatoms, e.g. a saturated or unsaturated aliphatic group, an aromatic group or a hydrocarbon group which has both aromatic and aliphatic parts. It is very particularly preferably a C1-C10-alkyl group, C1-C10-alkenyl group, e.g. an allyl group, a phenyl group or a benzyl group.

In a particular embodiment, the substituent is a C1-C10-, in particular C1-C4-alkyl group, e.g. a methyl group, ethyl group, propyl group, i-propyl group, n-butyl group, n-hexyl group, n-octyl group or n-decyl group.

The heterocyclic ring system is preferably an aromatic heterocyclic ring system.

The cation is preferably a derivative of imidazolium, of pyrazolium or of pyridinium.

The cation is particularly preferably a derivative of imidazolium (having two nitrogen atoms in the ring system and accordingly two of the above substituents).

The anion of the ionic liquid is preferably a compound having at least one carboxylate group (carboxylate for short) or at least one phosphate group (phosphate for short).

As phosphates, mention may be made of $PO_4^{3-}$ or organic compounds having a phosphate group, in particular dialkylphosphates. Particularly preferred phosphates are C1-C4-dialkylphosphates, e.g. dimethylphosphate and in particular diethylphosphate.

Preferred anions are carboxylates.

As carboxylates, particular mention may be made of organic compounds which have from 1 to 20 carbon atoms, preferably from 1 to 10 carbon atoms, and comprise from one to three carboxylate groups, preferably one or two carboxylate groups, particularly preferably one carboxylate group.

The compounds can be either aliphatic or aromatic compounds, with the term aromatic compounds referring to compounds which comprise aromatic groups. The aliphatic or aromatic compounds can optionally comprise further functional groups, e.g. hydroxyl groups, carbonyl groups or ether groups, or other heteroatoms, in particular halogens such as fluorine, chlorine or bromine, preferably fluorine, as substituent.

Very particular preference is given to aliphatic or aromatic compounds which do not comprise any further functional groups or heteroatoms apart from the oxygen atoms of the carboxylate group.

As compounds having two carboxylate group, mention may be made of, for example, the anions of phthalic acid, of isophthalic acid, of C2-C6-dicarboxylic acids, e.g. oxalic acid, malonic acid, succinic acid, glutaric acid or adipic acid.

As compounds having one carboxylate group, mention may be made of the anions of aromatic, aliphatic, saturated or unsaturated C1-C20-carboxylic acids, in particular alkanecarboxylic acids, alkenecarboxylic acids, alkynecarboxylic acids, alkadienecarboxylic acids, alkatrienecarboxylic acids, hydroxycarboxylic acids or ketocarboxylic acids. Suitable alkanecarboxylic acids, alkenecarboxylic acids and alkadienecarboxylic acids are also known as fatty acids.

Very particularly preferred carboxylates are the anions of C1-C10-alkanecarboxylic acids, in particular C1-C6-alkanecarboxylic acids, very particularly preferably acetic acid (acetate) and propionic acid (propionate).

Accordingly, the ionic liquid is particularly preferably an imidazolium salt of the formula I

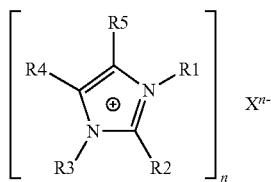

where

R1 and R3 are each, independently of one another, an organic radical having from 1 to 20 carbon atoms, R2, R4, and R5 are each, independently of one another, an H atom or an organic radical having from 1 to 20 carbon atoms, X is an anion and n is 1, 2 or 3.

Preference is given to R1 and R3 each being, independently of one another, an organic group comprising from 1 to 10 carbon atoms. The group is particularly preferably a hydrocarbon group which has no further heteroatoms, e.g. a saturated or unsaturated aliphatic group, an aromatic group or a hydrocarbon group which has both aromatic and aliphatic parts. The group is very particularly preferably a C1-C10-alkyl group, a C1-C10-alkenyl group, e.g. an allyl group, a phenyl group, a benzyl group. In particular, the group is a C1-C8-alkyl group, e.g. a methyl group, ethyl group, propyl group, i-propyl group, n-butyl group or octyl group.

Preference is given to R2, R4 and R5 each being, independently of one another, an H atom or an organic group comprising from 1 to 10 carbon atoms. R2, R4 and R5 are particularly preferably each an H atom or a hydrocarbon group which does not have any further heteroatoms, e.g. an aliphatic group, an aromatic group or a hydrocarbon group which has both aromatic and aliphatic parts. Very particular preference is given to an H atom or a C1-C10-alkyl group, a phenyl group or a benzyl group. Special preference is given to an H atom or a C1-C4-alkyl group, e.g. a methyl group, ethyl group, propyl group, i-propyl group or n-butyl group.

In a particular embodiment, R2 is not an H atom but has to be an organic radical as mentioned above having from 1 to 20 carbon atoms, in particular a C1-C4-alkyl group.

n is preferably 1.

X is preferably a carboxylate or phosphate, particularly preferably acetate or propionate.

As ionic liquids which are particularly suitable for the method of the invention, mention may be made of those having 1,3-dialkylimidazolium and 1,2,3-trialkylimidazolium cations (where alkyl=C1-C8) and an acetate or propionate anion, preferably an acetate anion.

Very particular preference is given to the propionates and in particular acetates of 1-methyl-3-ethylimidazolium, 1,3-diethylimidazolium, 1,3-dimethylimidazolium, 1-methyl-3-butylimidazolium, 1-ethyl-2,3-dimethylimidazolium 1,3-dioctylimidazolium; the phosphates of the above imidazolium cations, e.g. dioctylimidazolium phosphates, may also be mentioned as particularly preferred.

Their Mixtures

The mixtures to be distilled comprise the ionic liquids in any amount, they may for example consist of from 10 to 95% by weight of the ionic liquid. However, the content of ionic liquid in the mixture is preferably at least 5% by weight, particularly preferably at least 10% by weight, very particularly preferably at least 20% by weight, based on the total mixture; the process is also particularly suitable for mixtures having a content of at least 30 or 40% by weight of ionic liquid.

The content of ionic liquid is generally not greater than 95% by weight, usually not greater than 90% by weight or not greater than 80% by weight.

The ionic liquids can be present entirely or partly in dissociated form or in undissociated form (cation/anion pair formation). For carrying out the method of the invention, it is immaterial whether pair formation of anions and cations of the ionic liquid occurs in the liquid phase or whether the ionic liquid is present entirely or partly in dissociated form, e.g. in the presence of water or another hydrophilic or protic solvent.

Suitable mixtures for the method of the invention are, for example, mixtures comprising impurities and by-products resulting from the production process or the use of the ionic liquid.

The mixtures comprise, in particular, constituents having a boiling point above 200° C. (1 bar) as impurities, e.g. salts, natural or synthetic oligomers or polymeric compounds such as lignin, hemicellulose or oligosaccharides.

Mixtures from the Production Process

There are various processes for preparing ionic liquids. These processes usually give mixtures which comprise not only the ionic liquid but also undesirable by-products, starting materials and other impurities.

Mixtures suitable for the method of the invention are, for example, those obtained in the preparation of imidazolium salts by single-stage or multistage reaction of starting compounds selected from among: α-dicarbonyl compounds, amino compounds, carbonyl compounds, ammonia and carbonate compounds.

One production process is, for example, the carbonate method which is described in WO 2005/021484.

In the carbonate method, imidazolium salts are obtained by reacting an α-dicarbonyl compound, a carbonyl compounds (generally formaldehyde), an amino compound and ammonia in a first stage and subsequently reacting the reaction product with a carbonate (generally dimethyl carbonate) in a second stage. The mixture obtained after the first stage comprises by-products which make the total mixture appear dark to black.

Mixtures which are obtained after the first stage or after the second stage of the abovementioned production process are suitable for the method of the invention.

A further process for preparing imidazolium salts is described by Arduengo et al. (WO 91/14678, Arduengo process). In this single-stage process, the imidazolium salts are prepared by reacting an α-dicarbonyl compound, a carbonyl compound (generally formaldehyde) and an amino compound in the presence of an acid. Here too, the mixture obtained is dark to black because of by-products.

Mixtures obtained by this production process are suitable for the method of the invention.

Mixtures from Use

Mixtures obtained in the use of ionic liquids are likewise suitable for the method of the invention.

Ionic liquids are generally not consumed but only contaminated during use.

The use of ionic liquids therefore gives mixtures which comprise ionic liquids and impurities from the respective use. These mixtures can be worked up again by the method of the invention, so that the ionic liquid can be reused.

Ionic liquids are frequently used as solvents for substances which are insoluble or only sparingly soluble in other solvents. Ionic liquids are suitable, for example, as solvents for cellulose and cellulose-comprising materials. After the respective use of the solution, e.g. for producing cellulose fibers from the solution, mixtures which comprise ionic liquids and, for example, still some cellulose, lignin, hemicelluloses are obtained. The method of the invention is therefore particularly useful for mixtures which are obtained by dissolution and processing of cellulose or cellulose-comprising materials.

General Comments on Mixtures

According to the invention, the mixtures have added to them an organic compound (called distillation aid below) which is not ionic, has a molecular weight of less than 5000 and has a boiling point which is at least 5° C. higher (at 1 bar) compared with the ionic mixtures included in the mixture.

The molecular weight is preferably less than 4000, in particular less than 3000 and more preferably less than 2000 g/mol. The molecular weight is preferably greater than 200, in particular greater than 300 g/mol. In the case of pure compounds, the above molecular weight is the actual molecular weight of the distillation aid, or, if the substances present are mixtures, it is the number-average molecular weight Mn.

The distillation aid preferably has a boiling point which is at least 10° C., more preferably at least 20° C., higher than the boiling point of the ionic liquids present in the mixture.

The distillation aid is preferably miscible in any proportions with the ionic liquid present in the mixture.

The distillation aid is preferably an organic compound having ether or hydroxyl groups. With particular preference it is a polyether, which may optionally also comprise hydroxyl groups.

In one particular embodiment, the compounds in question are polyalkylene glycols or their monoesters or diesters or their monoethers or diethers, examples being their monoesters or diesters with low molecular weight carboxylic acids such as C1-C10 alkanecarboxylic acids, or their monoethers or diethers with C1 to C10 alkanols.

Particular preference is given to polyalkylene glycols, more particularly polyalkylene glycols of the formula HO—(R—O—)$_x$OH where R is a C1 to C4 alkylene group and x is an integer.

Very particular preference is given to polyethylene glycol.

Polyalkylene glycols of this kind, more particularly polyethylene glycol, are prepared typically by alkoxylation of glycol, generally giving mixtures with different degrees of alkoxylation; the molecular weights reported for the polyalkylene glycols are therefore number-average molecular weights Mn.

Especially preferred polyalkylene glycols, and polyethylene glycols, are those, for example, having a number-average molecular weight of more than 200, in particular more than 300. Particularly suitable are, for example, polyethylene glycols having a number-average molecular weight of 400 to 1000, especially 400 to 800.

The mixture comprises the distillation aid preferably in amounts from 0.5 to 40% by weight, in particular in amounts from 2 to 30% by weight, more preferably from 3 to 25% by weight. The amount of the distillation aid in the mixture in particularly preferred embodiments is 5 to 20% by weight or 10 to 20% by weight. The distillation aid may be added to the mixture at any desired point in time prior to the distillation.

The mixtures used in the method of the invention preferably comprise only minor amounts of volatile compounds.

For the present purposes, volatile compounds are compounds having a boiling point of less than 120° C., in particular less than 150° C., at atmospheric pressure (1 bar).

The content of volatile compounds is preferably from 0 to 10% by weight, in particular from 0 to 5% by weight and particularly preferably from 0 to 2% by weight and very particularly preferably from 0 to 1% by weight, based on the mixture.

If volatile compounds are initially present in the mixture, they are preferably largely removed so that their content in the mixture is not more than 10% by weight, in particular not more than 5% by weight, in particular not more than 2% by weight (see above), and are particularly preferably removed completely before carrying out the method of the invention.

The addition of a strong base as is described, for example, in DE 103 33 239 for producing purified imidazolium salts is not necessary according to the present invention. It is therefore preferred that no such strong base (pK$_B$ less than 0 at 1 bar, 21° C., measured in water) or no base at all is added to the mixture.

Distillation

The distillation is aimed at separating off and thus purifying the ionic liquids included in the mixture.

For distilling the mixtures comprising salts having a melting point of less than 200° C. at 1 bar (ionic liquids) a distillation in which the distance from the surface via which the heat of distillation is introduced in the distillation (vaporizer surface) to the surface at which condensation takes place (condenser surface) is less than 50 cm at least one point, with the vaporizer surface and condenser surface themselves having at least one length dimension of greater than 50 cm is suitable.

An important feature of the above distillation method is that the distance from the surface via which the heat of distillation is introduced in the distillation (vaporizer surface) to the surface at which condensation takes place (condenser surface) is less than 50 cm at least one point.

The vaporizer and condenser surfaces themselves have at least one length dimension greater 50 cm, i.e. these surfaces are large compared to the distance between them.

Distillation methods having a small distance between vaporizer surface and condenser surface are referred to as molecular distillation. In molecular distillation, the distance between vaporizer surface and condenser surface is generally less than the mean free path length of the compounds to the distilled. For this purpose, the geometry of the apparatus and the process parameters (pressure and temperature) are selected appropriately.

Any geometric arrangement of the condenser surface relative to the vaporizer surface in the apparatus is possible. The important thing is that these surfaces are directly opposite one another so that the molecules can travel unhindered from the vaporizer surface to the condenser surface.

Possibilities are, for example, parallel arrangement of two planar surfaces or a cylindrical arrangement in which two cylinders are placed within one another and the surfaces of the two cylinders which are directly opposite one another form the vaporizer and condenser surfaces.

The vaporizer surface is heated in a suitable way, generally by means of devices on the rear side; the condenser surface is generally cooled correspondingly, likewise by means of devices on the rear side.

The distance from the vaporizer surface to the condenser surface is less than 50 cm at at least one point, in particular less than 40 cm, particularly preferably less than 30 cm.

The distance from the vaporizer surface to the condenser surface is, in particular, less than the mean free path length of the ionic liquid in the gas phase at the chosen temperature and chosen pressure. The mean free path length ($\lambda_M$) can be determined by known methods and is given by the equation:

$$\lambda_M = \text{const} \times T/(p_\sigma^2)$$

where the symbols have the following meanings:
T: Temperature
P: Pressure
σ: Collision cross section of the ion pair (ionic liquid), corresponds to cross-sectional area of the ion pair Preferred suitable apparatuses are configured so that at least 10 percent by area, particularly preferably at least 20 percent by area, very particularly preferably at least 30 or even at least 50 percent by area, of the vaporizer surface have the above minimum distance from the condenser surface.

The vaporizer surface and the condenser surface can each be larger than 0.5 m², e.g. in the case of industrial-scale apparatuses.

In the method of the invention, the ionic liquid is separated off from the mixture and taken off as distillate from the condenser surface. The residue remains on the vaporizer surface. Suitable apparatuses are, for example, configured so that the residue runs off from the vaporizer surface and is collected, and the ionic liquid correspondingly runs off from the condenser surface and is obtained as distillate.

The surface temperature of the vaporizer and the pressure are preferably selected so that the distance between vaporizer surface and condenser surface is smaller than the free path length of the ionic liquid to be separated off in the gas phase.

The surface temperature is preferably from 110 to 300° C., particularly preferably from 130 to 280° C. and very particularly preferably from 140° C. to 260° C.

The pressure in the region between vaporizer surface and condenser surface is preferably from 0.0001 to 10 mbar, preferably from 0.001 to 5 mbar, particularly preferably from 0.05 to 5 mbar.

The method can be carried out continuously or batchwise. Corresponding apparatuses for continuous implementation are known. With such apparatuses, the mixture is supplied continuously at a particular feed rate, in which case the vaporizer surface must be designed in accordance with the feed rate such that the area and/or residence time of the mixture is sufficient for the desired removal.

The distillate obtained can, for example, comprise more than 95% by weight, particularly preferably more than 97% by weight, very particularly preferably more than 99% by weight, of the ionic liquid. In particular, distillates comprising more than 99.5% by weight or more than 99.8% by weight of the ionic liquid can also be obtained by means of the method.

It is therefore possible to obtain ionic liquids in high purity from any mixtures by means of the method of the invention. Through the use of the distillation aid, the residue as well remains liquid during the distillation, in particular, and this allows effective implementation of the distillation and effective removal of the ionic liquid. During the distillation, the residue remains of very high fluidity in the apparatus, and runs off over the vaporizer surface.

EXAMPLES

Ionic liquids (ILs) used
Abbreviations Chemical name
BMIM OAc 1-Butyl-3-methylimidazolium acetate
Mixtures for Distillation Ionic liquids which have previously repeatedly been used for the dissolution of cellulose (pulp from Tembec Inc. type 10A) and recovery of the cellulose by dilution with 10 times its amount of water (see WO 03/029329) are used as mixture. After each precipitation, the ionic liquid was recovered from the aqueous supernatant solution by distilling off the water at 120° C./1 mbar and was reused without further purification. It was freed of low boilers as described above before the molecular distillation. The ionic liquid fed to the distillation comprises about 6% by weight of secondary component (e.g. lignin) from the cellulose and is yellowish brown (Gardener color number=16).

To these mixtures were added the amounts of polyethylene glycol (PEG) specified in the table, the postpositioned number corresponding to the molecular weight (polyethylene glycol 400: number-average molecular weight 400 etc.).

Carrying out the Distillation

The contaminated ionic liquid used is freed of low boilers by stirring at 120° C. and 0.1 mbar for 16 hours before all distillation experiments in order to avoid foaming and spraying during the molecular distillation.

The distillation takes place in an apparatus for carrying out a molecular distillation. The ionic liquid is continuously fed to the apparatus and is evaporated on the vaporizer surface.

The distillate runs down on the condenser surface and is collected at the bottom, while the residue correspondingly runs down on the vaporizer surface and is collected at the bottom. The distillation was carried out continuously.

It was implemented under a reduced pressure of approximately 0.01 mbar.

The temperature of the condenser surface in all of the examples was 25° C.

The table reports the wall temperature (temperature of the vaporizer surface) and the feed rate in g/h (grams/hour).

Before the distillation is performed, it is advisable to determine—if not already known—the distillation temperature of the ionic liquid which is to be isolated from the mixture.

DISTILLATION EXAMPLES

Table 1 gives the figures for the composition of the mixtures; table 2 gives figures relating to the implementation of the distillation.

TABLE 1

| Example No. | IL | Polyethylene glycol (PEG) | Polyethylene glycol (PEG) % by weight |
|---|---|---|---|
| 1 | EMIM-OAc | — | — |
| 2 | EMIM-OAc | PEG 400 | 5 |
| 3 | EMIM-OAc | PEG 400 | 16 |
| 4 | EMIM-OAc | PEG 600 | 17 |

TABLE 2

| Example No. | Wall temperature (°C.) | Feed rate g/h | Flow behavior of residue |
|---|---|---|---|
| 1 | 180 | 45 | − |
| 2 | 195 | 67 | +− |
| 3 | 210 | 194 | + |
| 4 | 200 | 232 | + |

The flow behavior was assessed as follows in 3 stages:
− residue highly viscous, poor fluidity
+− improved fluidity
+ high fluidity of the residue

The invention claimed is:

1. A method of distilling an ionic mixture, the method comprising adding to an ionic liquid a distillation aid and distilling the ionic mixture by a molecular distillation method, wherein:
the ionic liquid comprises at least one salt, which is composed of at least one cation and at least one anion and has a melting point of less than 200° C. at 1 bar, and
the distillation aid comprises an organic compound which:
is not ionic,
has a molecular weight of less than 5000, and
has a boiling point which is at least 5° C. higher compared with ionic components within the ionic mixture.

2. The method of claim 1, wherein the cation of the ionic liquid comprises a heterocyclic ring system with at least one nitrogen atom, wherein the at least one nitrogen atom has bonded to it an organic substituent.

3. The method of claim 1, wherein the cation is an imidazolium cation.

4. The method of claim 1, wherein the organic substituent on the at least one nitrogen atom is a C1-C10-alkyl group.

5. The method of claim 1, wherein the ionic liquid is an imidazolium salt of the formula I:

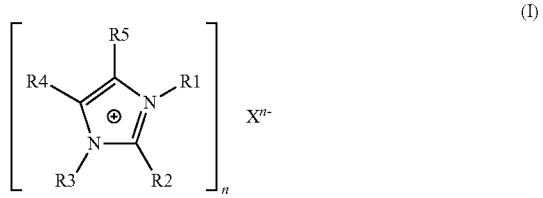

wherein:
R1 and R3 are each, independently of one another, an organic radical having from 1 to 20 carbon atoms,
R2, R4, and R5 are each, independently of one another, a H atom or an organic radical having from 1 to 20 carbon atoms,
X is an anion, and
n is 1, 2 or 3.

6. The method of claim 5, wherein R2 is an organic radical having from 1 to 20 carbon atoms.

7. The method of claim 1, wherein the at least one anion is a compound having at least one carboxylate group or at least one phosphate group.

8. The method of claim 1, wherein the ionic mixture comprises from 10 to 95% by weight of the ionic liquid.

9. The method of claim 1, wherein the ionic mixture is obtained in the preparation of the ionic liquid by single-stage or multi-stage reaction of at least one starting compound selected from the group consisting of a α-dicarbonyl compound, an amino compound, a carbonyl compound, ammonia and a carbonate compound.

10. The method of claim 1, wherein the ionic mixture is obtained from the ionic liquid.

11. The method of claim 1, wherein the ionic mixture comprises at least one further constituent with a boiling point above 200° C. (1 bar) as an impurity.

12. The method of claim 1, wherein the organic compound comprises at least one ether group or at least one hydroxyl group.

13. The method of claim 1, wherein the distillation aid is a polyether, which may optionally further comprise at least one hydroxyl group.

14. The method of claim 1, wherein the distillation aid is a polyalkylene glycol.

15. The method of claim 1, wherein the amount of the distillation aid in the ionic mixture is from 0.5 to 40% by weight, based on the total weight of the ionic mixture.

16. The method according to claim 1, wherein, in the distilling, the distance from the surface of heat introduction (vaporizer surface) to the surface of condensation (condenser surface) is less than 50 cm from at least one point, and the vaporizer surface and the condenser surface each have at least one length dimension of greater than 50 cm.

17. The method of claim 1, wherein more volatile compounds in the ionic mixture, which have lower boiling points than the ionic liquid in the ionic mixture, are separated off before distilling so that their proportion in the ionic mixture is not more than 10% by weight.

18. The method of claim 16, wherein at least 10 percent by area of the vaporizer surface is at a distance of less than 50 cm from the condenser surface.

19. The method of claim 16, wherein the vaporizer surface and the condenser surface are each larger than 0.5 m$^2$.

20. The method of claim 16, wherein the distilling is carried out such that the surface temperature of the vaporizer surface is from 110° C. to 300° C. and the pressure is from 0.0001 to 10 mbar.

21. The method of claim 1, wherein a distillate obtained comprises more than 97% by weight of the ionic liquid.

22. The method of claim 11, wherein the at least one further constituent is selected from the group consisting of a natural oligomeric compound, a synthetic oligomeric compound, a natural polymeric compound, a synthetic polymeric compound, a lignin, a hemicellulose, and an oligosaccharide.

23. The method of claim 1, wherein the distillation aid is a polyethylene glycol.

24. The method of claim 17, wherein the proportion of the more volatile compounds in the ionic mixture is not more than 5% by weight.

* * * * *